United States Patent [19]

Silver, III

[11] 4,246,344

[45] Jan. 20, 1981

[54] METHOD OF DETECTING ADHERENT CELLS

[75] Inventor: Spencer F. Silver, III, White Bear Lake, Minn.

[73] Assignee: Minnesota Mining and Manufacturing Company, St. Paul, Minn.

[21] Appl. No.: 28,349

[22] Filed: Apr. 9, 1979

[51] Int. Cl.³ .............................................. C12Q 1/06
[52] U.S. Cl. ......................................... 435/39; 73/23; 73/61 R; 310/311
[58] Field of Search .................... 73/23, 61 R; 435/4, 435/29, 30, 39; 23/230 B

[56] References Cited

U.S. PATENT DOCUMENTS

| | | | |
|---|---|---|---|
| 3,164,004 | 1/1965 | King, Jr. | 73/23 |
| 3,329,004 | 7/1967 | King, Jr. | 73/23 |
| 3,653,253 | 4/1972 | Olin | 73/61 R X |
| 3,715,911 | 2/1973 | Chuan | 73/23 X |
| 3,856,466 | 12/1974 | Crawford | 73/23 X |
| 3,879,992 | 4/1975 | Bartera | 73/23 X |
| 3,895,912 | 7/1975 | Naumann | 73/23 X |
| 3,999,944 | 12/1976 | Grosser et al. | 23/230 B |

OTHER PUBLICATIONS

Alan Schons et al., An Immunospecific Microbalance, Journal of Biomed. Mater. Res., vol. 6, pp. 565–570; 1972.

Primary Examiner—Robert J. Warden
Attorney, Agent, or Firm—Cruzan Alexander; Donald M. Sell; Carolyn A. Bates

[57] ABSTRACT

A method is disclosed for the direct quantitative measurement of adherent cells in a liquid sample. The method consists of contacting and incubating the sample with a piezoelectric oscillator having a premeasured resonant frequency, washing and drying the oscillator and determining its change in frequency.

24 Claims, No Drawings

METHOD OF DETECTING ADHERENT CELLS

This invention relates to an improved method for detecting the number of adherent cells in a sample containing a population of viable cells. Determination of the adherency of certain types of cells is useful in the diagnosis of various biological disorders of the human body.

It is well known that leukocytes and blast cells have a degree of adherency or adhesiveness to glass, glass wool, nylon wool, cotton wool, plastic or other surfaces. See, for example, Bubenik et al, "The Latex Particle Adherence (L.P.A.) Assay for Detection of Leukocytes with Adhesive Surface Properties," Cellular Immunology 35, 217 (1978).

The term leukocyte refers to a mixture of white blood cell types obtained from peripheral blood, lymph or organs such as the thymus, spleen or lymph nodes and peritoneal exudate. The term mononuclear cell refers to those leukocytes separated by a density gradient technique, usually employing, for example, LSM ® solution (lymphocyte separating medium, a mixture of sodium metriazoate and epichlorohydrin-sucrose polymer), and consisting of lymphocytes and monocytes (also known as macrophages when found in tissue). Monocytes (macrophages) are large, adherent highly phagocytically active mononuclear cells. Lymphocytes are relatively small nondescript cells responsible for antibody production and capable of becoming cytotoxic cells with proper stimulation. The other major type of leukocytes are the granulocytes, also characterized as polymorphonuclear cells (PMN'S); Neutrophil refers to the most common type of granulocyte in peripheral blood and is characterized by its ability to phagocytize foreign bodies. All of these cells are identified primarily by histologic staining techniques and their behavior during density gradient sedimentation. These cells, in particular those that are phagocytic, are known to be adherent to various surfaces by either "active adherence" requiring a metabolically active cell or "physical adherence" which does not require cells to be capable of active metabolism yet the cells must be viable.

The ability of a particular cell or group of cells to adhere to a surface is of diagnostic utility. MacGregor et al (J. Clin. Imm. 57, 1098-1103 (1976)) have found granulocyte adherence in vitro to be enhanced during acute inflammatory disease, and furthermore, the effect of anti-inflammatory drug therapy can be monitored by adherence measurement. Stecher et al (Agents Action 8, 258-62 (1978)) has also evaluated granulocyte adherence as having potential for detecting anti-inflammatory agents not normally effective in standard animal models. Inhibition of leukocyte adherence to various surfaces in the presence of tumor antigens has been demonstrated by several groups (Halliday et al, Cancer Res. 37 1962-77)) and its application to the diagnosis of some types of cancer (colorectal and melanoma) may be warranted. Enhanced leukocyte adherence in the presence of microbial antigens derived from bacillus Calmette-guerin (BCG) has been shown (Bullen et al, Clin. Exp. Immunol. 31, 408-13 (1978)). This result is unusual in that it is opposite from the response observed with tumor antigens. U.S. Pat. No. 3,999,944 describes a method for detecting breast cancer in humans by determining leukocyte adherence inhibition in the presence of exogenous antigen (breast tumor extract) compared to controls. T. T. O'Flaherty et al (Am. J. Pathol. 90. 537-50 (1978)) have shown that human neutrophils and monocytes respond to chemotactic factors by developing a hyperadherent cytoplasmic membrane.

There are several methods for estimating a population of adherent cells currently in practice. The most straight-forward method involves allowing whole blood or leukocyte preparations to percolate through small columns containing various materials such as nylon wool, cotton wool or glass beads. In these cases the number of adherent cells is inferred by counting the number of cells before and after passage using either a hemacytometer or Coulter Counter ® apparatus. For dilute cell suspensions, glass test tubes are used as the adherent surface. These techniques suffer from many disadvantages including loss of cells by physical entrapment within the column, destruction of fragile cells during the filtration process, difficulties in reproducibly packing columns with the fibrous materials, problems of differential adsorption of the several cellular species present and ultimately the problems of having a rely on visual method of cell counting. To overcome many of these problems, some authors (Bubenik, supra) have proposed measuring adherent cells by counting the number of tiny latex beads which attach to surface of the cell. This process introduces a substantial risk due to human error since the endpoint is visually observed. It has also been recognized that erroneous counts can arise from such variables as the diluting buffer, mixing procedures and mixing vessel.

Leukocyte adherence (or inhibition of adherence) has also been detected by measuring the migration of cells out of capillary tubes. (Bullen et al, Clin. Exp. Immunol. 31 408-13 (1978)). The size of the migration pattern is compared with controls and given a subjective rating depending upon extent or size of the migration pattern.

Instrumental methods of analysis are rendered difficult by virtue of the fact that adherent cells attach to containers thereby causing the results to be dependent upon the amount of vessel surface to which a dispersion has been exposed during the assay. As a result of the aforementioned difficulties, resort has been primarily to visual means of measurement. Such measurements are time-consuming and of questionable accuracy.

The present invention overcomes the aforementioned problems associated with the accurate measurement of adherent cells. It provides an instrumental method which eliminates the subjectiveness and human error of visual counting. The method is very simple to perform, requires unsophisticated and inexpensive equipment and avoids excessive pipetting, mixing procedures or dilutions which introduce errors by depleting a cell suspension of adherent species through excessive contact with surfaces to which the cells naturally adhere.

According to the present invention there is provided a method for the direct and quantitative measure of the number of adherent cells in a liquid sample comprising the steps of: (1) contacting the liquid sample containing cells with a piezoelectric oscillator having a premeasured frequency; (2) incubating for a predetermined length of time; (3) washing and drying the oscillator; and (4) determining the change in frequency of the oscillator.

Since the method is a direct measure of adherent cells, it is exquisitely sensitive and as such, it is well within the scope of the invention to detect a single adherent cell. There is no other technique, manual or automated, capable of this sensitivity on a routine basis.

This method may be used for measuring or detecting in a direct, quantitative manner, an adherent population of cells, in particular those cells with known adherent properties, viz. leukocytes, mononuclear cells, granulocytes or specifically neutrophils, monocyte/macrophage, lymphocytes and/or blast-stage cells. Other types of cells considered detectable within the scope of the invention include fibroblasts, platelets, etc.

As a further aspect of invention, the oscillator surface can be modified by coating with various polymeric materials or otherwise modified to achieve selective adherence in mixed cell populations.

Evaluation of cell adherence as determined by the present method may be used as a means of assessing the biological or, more specifically, the immunological competence of the organism from which the cells were obtained. Subsequently, such information may be utilized to diagnose the presence of tumors, bacterial, parasitic or fungal infection, estimation of organ transplant rejection, etc.

Piezoelectric oscillators are commonly used in electronic equipment or clocks as frequency standards and controllers. Generally, they consist of a small quartz wafer (or other material), having metal electrodes deposited on either side and some means provided for making electrical contact with an oscillator circuit. When placed in such a circuit, the portion of the wafer located between the electrodes vibrates with the precise natural frequency of the wafer. A given mass coupled to the electrode of the oscillator (used interchangeably with "crystal") herein causes a decrease in the initial frequency of the oscillator in an amount proportional to the mass added. The mass being detected must be uniformly distributed over a given area of the quartz plate. This requirement was stated as stringent by Warren and Stockbridge (Vacuum Microbalance Techniques, Vo. 2, p. 72, Plemum, New York, N.Y.). These authors furthermore state that the field of usefulness is limited to those materials which can be uniformly bonded to the quartz plate. King (Research/Development, April, 1969) states that any axial motion outside of the axial motion of the oscillator (as would be the case in a cellular "bag of jelly") results in a bad or poor oscillator. Furthermore, if the film coated on a crystal is uneven or bumpy, a poor resonator also results, and in some instances the resonant point cannot be determined. Oscillators coated with thin films of Apiezon-L ® stopcock grease have been used to analyze for particles in air, however, particle loadings of only 400 Hz (10 MHz crystal) gave a nonlinear frequency response, with the crystals becoming saturated at 2000 Hz, i.e. they did not oscillate (F. W. Karasek, Industrial Research/Development, October, 1978, p. 156).

Surprisingly, the method of the present invention may be used to accurately determine the number of cells which adhere to the surface of the crystal by resonance changes even though the cell or cells may not be uniformly attached and also contain material which moves independently of the crystal.

Piezoelectric oscillators have been used heretofore in the medical diagnostic art. Shons et al (J. Biomed. Mater. Res. 6, 565–157 (1970)), describe a direct method for measuring the amount of an antibody in a liquid sample using a piezoelectric quartz crystal. The crystal is first coated with the antigen specific for the antibody being assayed and its frequency measured. The coated crystal is then exposed to the sample containing the antibody. The change in frequency of the crystal due to antibody pickup is a direct measurement of the amount of antibody in the sample.

An indirect method for determining the amount of an antigen in a liquid sample is disclosed in copending application Ser. No. 851,491, filed Nov. 14, 1977 assigned to the same assignee as the present application. An antigen pre-coated piezoelectric oscillator is exposed to a sample containing the antigen and a predetermined amount of antibody specific for the antigen. The antigen attached to the crystal competes with the antigen in the sample for the supply of antibody. The change in frequency of the piezoelectric oscillator is compared to a reference curve, and the amount of antigen in the sample is indirectly determined.

The present invention utilizes the piezoelectric oscillator to measure directly the number of adherent cells in a cell suspension.

Oscillators having various surface properties can be used in a number of different assays according to the invention: (1) bare, cleaned crystals wherein the cells adhere to the bare metal electrodes; (2) charge-modified surfaces in which the surface has a substantial positive or negative character such as that provided by an adsorbed monolayer of, e.g., poly(2-hydroxy-3-dimethylamino-1,4-butane) (described in copending application Ser. No. 851,492, filed Nov. 14, 1977 and assigned to the same assignee as the present application); a positively charged material or gum arabic, a negatively charged material. (3) hydrophobic or electrically neutral surfaces such as that provided by a layer of a polymer such as polystyrene; and (4) proteinaceous surfaces where a monolayer of a specific protein has been adsorbed on a primed surface. These surfaces can be used in a variety of ways. For example, cells are known to have varying surface charges depending on cell type. Charged surfaces can be used to detect individual subsets of cells in a mixed population. Neutral or hydrophobic coatings (including bare metal electrodes) provide a reproducible and uniformly nonspecific adherent surface most useful for comparing normal and abnormally responsive cells. Proteinaceous surfaces provide the means for detecting cells via their cell surface markers or cell membrane receptors. A notable example of the latter is the response of neutrophils to opsonized* surfaces.

*Opsonin: A serum substance, usually an antibody, which coats particulates such as bacteria, to promote phagocytosis.

The method of determining adherent cells according to the present invention is carried out as follows: (1) the oscillator frequency is first determined; (2) the oscillator is mounted horizontally in any convenient manner; and (3) a droplet of leukocyte cell suspension containing about $10^6$ cells/ml of buffer is placed on the surface of the oscillator. Any commonly used buffers for cell culture may be used, which may also contain fetal calf serum. The cell suspension at this point may also contain autologous serum proteins or antigenic material, i.e., tumor antigens, or the like, depending on the particular type of assay being conducted. Cell suspension concentration is generally in the range of $10^5$–$10^7$ cells/ml, however, other concentrations are possible depending on the cell's propensity for adherence (or incubation time).

The droplet plus crystal is then incubated at room temperature or 37° C. for a predetermined period of time (usually 30 to 60 minutes). The surface of the oscillator is then washed with distilled water optionally containing 100 ppm $Ca^{+2}$, dried and the final resonant frequency determined. The frequency shift is a measurement of the number of cells adhered to the crystal per unit area and can thus be correlated with the number of adherent cells present by reference to standard curves.

If the size and density of cells are known then the number of adherent cells can be calculated directly using the Sauerbrey equation*, $$\Delta F = 2.3 \times 10^6 F^2 \frac{(\Delta W)}{(A)}$$

where $\Delta F$ = frequency change due to the coating, Hz; $\Delta W$ weight of deposited film, grams;** and A = area of the electrode, cm.

*Sauerbrey, G., Z. Phyzik 178, 457 (1964)
**F = Fundamental frequency of the quartz plate, MHz.

The cell becomes mechanically coupled to the surface of the crystal. Cells simply lying on the surface or otherwise not attached cannot be detected by this method. Thus, the invention detects only cells capable of the specific interaction, due either to the cell type or the surface character, or interactions of cell surface receptors with prepared crystal oscillators.

The method of this invention can be used to assay for virtually all adherent cell types of all species including neutrophils, eosinophils, basophils, monocyte/macrophage, lymphocytes, etc. The invention is further illustrated by the following nonlimiting examples.

EXAMPLE 1

Preparation of Leukocytes and Fractionation into Subgroups

Twenty milliliter samples of heparinized (10–20 units/ml) venous blood were mixed with 10 ml of 6% Dextran 70 in 0.9% saline (Cutter Labs., Inc.) and placed vertically in a 50 cc plastic syringe at room temperature for about one hour to sediment out red blood cells. (Alternatively, whole heparinized blood is first spun at $140 \times g$ for ten minutes and the plasma, buffy coat and topmost layer of red cells removed and diluted with medium. Leukocytes were then collected by centrifugation of the plasma layer at $150 \times g$ for ten minutes. The cell pellet was suspended in 3 ml of distilled water for 20 seconds in order to lyse any contaminating red cells, after which 1 ml of 4× saline was rapidly added. The cells were recovered by centrifugation, mixed with 8 ml MEM (Minimum essential medium, Eagle, Grand Island Biological Co.), pH 7.2, containing 25 mM HEPES (N'-2-hydroxyethylpiperazine-N'-ethanesulfonic acid), layered over 3 ml LSM (Lymphocyte Separating Medium, Bionetics Laboratory Products) solution and centrifuged at $400 \times g$ for 35 minutes. The interfacial layer of cells, which consists of mononuclear cell types, was removed by aspiration and washed by centrifugation ($450 \times g$, 10 min.) three times with MEM-HEPES. A cell count was done and the final concentration of cells adjusted to $1-5 \times 10^6$ cells/ml in MEM.HEPES. Trypan blue dye exclusion generally showed >95 percent viable cells (human samples).

The granulocyte fraction was isolated by decanting the remaining LSM, suspending the cell pellet in MEM-HEPES and washing the recovered cells three times with MEM-HEPES. The final concentration of granulocytes was adjusted to $1-5 \times 10^6$ cells/ml in MEM-HEPES. This fraction generally consisted of 75% or greater neutrophils with the remainder being lymphocytes and monocytes as determined by Wright stained Centocentrifuge® cell preparation (Shanden-Southern Products Ltd., Cheshire, England). Generally, more than 95% of the granulocytes were viable as determined by dye exclusion (human samples).

EXAMPLE 2

Relationship of Adherence (Frequenty Shift) to Cell Suspension Concentration

Quartz crystal oscillators (10 MHz, AT-cut; 7.5 mm diameter wafer, 5 mm diameter electrodes*) coated with human serum albumin were used. These were prepared as follows: twelve crystals were clenaed by soaking for one hour in 10% trisodium phosphate, thoroughly rinsed with water and then primed by soaking overnight in a 0.06–0.08% aqueous solution of poly(2-hydroxy-3-dimethylamino-1,4, butane)(DiMA). The crystals were washed, dried and a monolayer of human serum albumin (HSA, Sigma) was applied by soaking four hours at room temperature in a 5 mg/ml solution of HSA in 0.02 M phosphate buffer, pH 7.0. After washing with distilled water and drying with a nitrogen stream, the crystals were found to have adsorbed a monolayer of HSA corresponding to a mean frequency shift of 241 Hz.

*The standard oscillator for all the assays reported herein unless otherwise specified.

The assay was carried out in triplicate by adding a 50 microliter ($\lambda$) droplet of cell suspension in MEM, pH 7.2 in concentrations shown in Table I, to the surface of each of three horizontally mounted crystal oscillators. After a 30 minute incubation at room temperature, unattached cells were rinsed off with 50 ml of distilled water and the crystals dried before determining their final frequency. The relationship of cell adherence to frequency shift for this experiment is given in Table I.

TABLE I

| Crystal No. | Cell Concentration | $\Delta F$ (Hz) | Average $\Delta F$ (Hz) |
|---|---|---|---|
| 1 | $7.6 \times 10^6$ | discarded | |
| 2 | " | 6265 | 5927 |
| 3 | " | 5588 | |
| 4 | $6.0 \times 10^6$ | 4270 | |
| 5 | " | 4526 | 4885 |
| 6 | " | 5860 | |
| 7 | $3.8 \times 10^6$ | 253 | |
| 8 | " | 593 | 665 |
| 9 | " | 1149 | |
| 10 | $1.8 \times 10^6$ | 368 | |
| 11 | " | 329 | 383 |
| 12 | " | 451 | |

EXAMPLE 3

Relationship Between Adherence as Measured by Frequency Shift and Viability of a Given Cell Preparation Rabbit peripheral blood granulocytes (whose viability is rapidly lost with time) prepared according to Example 1 were used in this experiment. Final cell concentration was $2.4 \times 10^6$ cells/ml in Hank's balanced salt solution (HBSS) (with $HCO_3^-$), pH 7.2. Viability at t=0 was 82% as determined by Trypan blue dye exclusion. Ten MHz crystals were precoated by briefly dipping in a 1% solution of polystyrene in toluene after which the crystals were blown dry in a stream of nitrogen. These crystals were kept at room temperature for 24 hours before use to allow any residual solvent to evaporate. The cell suspension was assayed at one hour intervals by placing a 50 $\lambda$ droplet of the suspension on the surface of each of three horizontally mounted crystal oscillators and incubating 30 minutes at room temperature in a humid chamber. The crystals were then washed on the top surface only with 50 ml distilled water and dried in a stream of nitrogen. The change in frequency after contact with cells was found to correlate with viability as shown in the following Table II.

TABLE II

| Post Harvest Time Interval (hours) | ΔF (Hz) | ΔF (Hz) Average | % Viable Cells |
|---|---|---|---|
| 0 | 3658 | | |
| | 2606 | 3110 | 82 |
| | 3067 | | |
| 1 | 1262 | | |
| | | 1390 | 61 |
| | 1477 | | |
| 2 | 812 | | |
| | 869 | 1012 | 12 |
| | 1357 | | |
| 3 | 1078 | | |
| | | 925 | 13 |
| | 772 | | |
| 24 | 488 | | |
| | | 486 | 12 |
| | 484 | | |

Control crystals treated as described above except media containing no cells were used showed an average of 30 Hz weight loss.

EXAMPLE 4

Relationship Between Cell Adherence and Time of Contact with Crystal

The granulocyte fraction of human leukocytes was prepared according to Example 1. The final suspension contained $5.5 \times 10^6$ cells/ml in MEM-HEPES, pH 7.2. The cells were 99% viable as determined by Trypan blue dye exclusion. Polystyrene coated 10 MHz crystal oscillators were prepared by dip coating in a dilute solution of the polymer in toluene as described in Example 3. Oscillator frequency was determined immediately before adding the cell suspension.

Ten coated crystal oscillators were mounted horizontally and a 50 λ droplet of cell suspension placed on the surface of each crystal. Pairs of crystals were then washed with 50 ml water at the time intervals indicated in the following Table III. After drying, the final frequency was determined and frequency shift calculated. Increase in adherent cells (ΔF) with time was found to reach a maximum after about 40 minutes.

TABLE III

| Crystal No. | ΔTime (min.) | ΔF (Hz) | ΔF (Hz) Average |
|---|---|---|---|
| 1 | 10 | 3830 | |
| | | | 5183 |
| 2 | " | 6536 | |
| 3 | 20 | 6404 | |
| | | | 7500 |
| 4 | " | 8596 | |
| 5 | 30 | 6321 | |
| | | | 8108 |
| 6 | " | 9894 | |
| 7 | 40 | 11792 | |
| | | | 11623 |
| 8 | " | 11453 | |
| 9 | | Lost | |
| 10 | 60 | 10764 | 10764 |

EXAMPLE 5

Use of Crystal Oscillators to Determine Phagocytic Function of Granulocytes

Human granulocytes were isolated according to Example 1. The final cell suspension was $5.1 \times 10^6$ cells/ml in MEM-HEPES, pH 7.2. Polystyrene-coated crystal oscillators were prepared as described in Example 3. Particles for phagocytosis were prepared by: (1) diluting a 5% polystyrene latex (d=0.82μ, Polysciences) 1:1500 with MEM-HEPES, pH 7.2 that contained 10% autologous serum; and (2) dispersing 2 mg zymosan starch granules (Sigma Chemical Co.) in MEM-HEPES, pH 7.2, that contained 10% autologous serum. These particle suspensions were calculated to provide ten particles/cell during the phagocytosis assay.

For the assay, a 0.5 ml sample of the appropriate particle suspension was mixed with 0.5 ml of the cell suspension. The particle-cell mixture was then incubated with shaking for 60 minutes in a 37° water bath. After the incubation, a 50 λ droplet was added to the surface of each of two horizontaly mounted crystal oscillators having premeasured frequencies and the crystal left at room temperature in a humid chamber for 60 minutes. Controls consisted of crystals treated with cells plus autologous serum with no particles and cells in medium alone. The crystals were washed in the usual manner and the final frequency determined. Results are shown in the following Table IV.

TABLE IV

| | ΔF (Hz) | ΔF (Hz) Average |
|---|---|---|
| Cells + zymosan (10% autologous serum) | 3422 | 3335 |
| Cells + 0.82 μ latex (10% autologous serum) | 4890 | |
| | 7968 | 6429 |
| Cells + autologous serum | 12152 | |
| | 11227 | 11884 |
| | 12272 | |
| Cells only | 5269 | |
| | 6194 | 4414 |
| | 1778 | |

Microscopic examination of the cell-particle suspensions showed extensive incorporation of particles within cells, the cells becoming highly vacuolated (frothy appearance).

These data indicate that a decrease in adherence accompanies phagocytosis and thus the assay can be used to estimate phagocytic ability (or competence) of a population of cells.

EXAMPLE 6

Effect of Opsonizing Crystals and the Resulting Enhancement of Cellular Response Rabbit granulocytes from peripheral blood were prepared according to Example 1. These rabbits had been previously sensitized to whole bee extract by a 2 ml subcutaneous injection of a 10 mg/ml dispersion of whole bee extract in complete freunds adjuvant plus a boost at one month with 2 ml at 2 mg/ml in complete Freunds. The final cell suspension concentration was $1.8 \times 10^6$ cells/ml in HBSS. Crystal oscillators were prepared by first priming with DiMA as described in Example 2 and then attaching a monolayer derived from whole bee extract (Hollister-Stier). The whole bee extract (WB) was prepared prior to adsorption by dialyzing against excess 0.01 M phosphate, pH 7.0, overnight at 4° C. and the contents of the dialysis bag diluted 1:10 with 0.02 M phosphate buffered saline, pH 7.0. A control surface having bovine serum albumin (BSA) as a surface layer was prepared by adsorption on DiMA primed crystals from a BSA solution in phosphate buffer, pH 7.0 as described in Example 2. The initial frequency of the crystals was determined immediately before use. The crystals were then mounted horizontally and opsonized by applying a droplet of autologous serum. After incubation, the droplet was removed and a 50 λ droplet of cell suspension added to the crystal. The crystals were incubated at room temperature for 30 minutes washed in the usual manner and the final frequency determined. The results are shown in Table V.

TABLE V

| Sample | Opsonizing Serum | ΔF (Hz) | ΔF (Hz) Average |
|---|---|---|---|
| WB-Treated crystal | + | 3668 | |
| | | 3851 | 3841 |
| | | 4005 | |
| WB-Treated crystal | − | 2010 | |
| | | 1787 | 1859 |
| | | 1782 | |
| DiMA-treated crystal (control) | + | 1994 | |
| | | 2251 | 2051 |
| | | 1908 | |
| BSA-Treated crystal (control) | − | 1395 | 1395 |

The greater than 100% increase in adherence of cells to crystal oscillators in the presence of opsonizing serum indicates that substituents in the autologous serum recognize the surface as foreign, bind, and thereby enhance the cellular interaction.

Whole bee extract is only one example of an antigen layer which can be coated onto the oscillator prior to contacting the oscillator with the cell sample. Other antigens may include viral antigens, parasitic antigens, fungal antigens, tumor antigens, antigenic products of viruses, antigenic products of parasites, antigenic products of fungi, antigenic products of tumors and plant-derived lectins. The antigen layer may also be a contact dermatitis antigen or an autoimmune disease-associated antigen.

EXAMPLE 7

Response of Granulocytes Obtained from Healthy Human Volunteers to Common Microbial Antigen Preparations in the Presence of Serum Human granulocytes were prepared as described in Example 1. These cells were used in the assay at $5 \times 10^6$ cells/ml in MEM-HEPES, pH 7.2, 10% in fetal calf serum as a stabilizer. Cell viability was greater than 98% as determined by Trypan blue dye exclusion. Microbial antigens were derived from 69-86 hour cultures at 37.5° C. in MEM. These cultures were centrifuged and filtered through a 0.45μ filter to remove all particulate matter and used immediately. The crystal oscillators were prepared by first priming with DiMA as described in Example 2, followed by soaking the crystals batchwise in the appropriate culture filtrate for 8 hours at room temperature. The crystals were then washed and dried and the frequency shift corresponding to the amount of material adsorbed from the microbial antigen preparation determined. Control samples having human serum albumin (HSA) adsorbed were prepared as described in Example 2.

Frequency shifts related to microbial antigen coatings were found to vary depending upon the length of time of the bacteria were cultured, however, the following ΔF data are representative: HSA (207 Hz); E. coli (690 Hz); S. aureus (280 Hz); P. aeruginosa (102 Hz); K. pneumoniae (159 Hz); and H. vaginalis (735 Hz).

For the assay, the initial frequencies of the crystal oscillators were determined and the crystals mounted horizontally. The granulocyte suspension was made 10% in autologous serum (or MEM added for controls) and a 50 λ droplet of this mixture was added to the surface of each crystal. After incubating at room temperature for 30 minutes, the crystals were washed with 50 ml of water containing 100 ppm $CaCl_2$, dried and the final frequency measured.

TABLE V

| | Response of Neutrophils to Microbial Antigen Coated Crystals | | | | | |
|---|---|---|---|---|---|---|
| | Average ΔF(Hz) | | | | | |
| | Donor A | | Donor B | | Donor C | |
| Microbial Antigen From: | Control** | Serum | Control | Serum | Control | Serum |
| HSA* | 1806 | 2137 | 1375 | 2898 | 4530 | 4743 |
| E. coli | 496 | 3630 | 502 | 5706 | 4312 | 13849 |
| S. aureus | 2712 | 3686 | 1132 | 329 | 4291 | 9152 |
| P. aeruginosa | 1137 | 1774 | 681 | 11547 | 3617 | 17085 |
| K. pneumoniae | 634 | 6486 | 724 | 10683 | 5271 | 8436 |
| H. vaginalis | 402 | 15574 | 772 | 15980 | 2473 | 21324 |

*Control surface.
**No autologous serum present in controls.

Comparison of experimental samples with the control surface, HSA, in the presence of serum shows enhanced granulocyte adherence is observed using the method of the present invention.

EXAMPLE 8

Use of Quartz Crystal Oscillators to Determine the Chemotactic Activity of Granulocytes Human granulocytes were isolated according to Example 1. The final cell suspension was $8.5 \times 10^6$ cells/ml in MEM-HEPES, pH 7.2, containing 10% autologous serum. Polystyrene treated crystal oscillators were prepared as described in Example 3. For this experiment a series of N-formylmethionylphenylalanine (FMP, Andrulis Research Co., Bethesda, Md.) solutions ranging from $10^{-3}$ to $10^{-7}$ M in MEM-HEPES were prepared immediately before use.

For the assay, a 20 λ droplet of FMP solution was first placed on a horizontally mounted polystyrene coated crystal and a 5μ Nucleopore$^R$ membrane, 6.5 mm in diameter, placed (floated) on top of the FMP solution. A 50 λ droplet of cell suspension was then placed on top of the membrane. The composition was incubated for 4 hours at room temperature in a petri dish with moitened filter paper. Following incubation the membrane was removed with forceps and the crystal washed in the usual manner and final frequency determined. The results are shown in Table VI.

TABLE VI

| Chemotactic Factor | ΔF (Hz) | Average ΔF (Hz) |
|---|---|---|
| $10^{-3}$ M FMP | 8556 | 10219 |
| | 11882 | |
| $10^{-4}$ M FMP | 4969 | 6886 |
| | 8802 | |

TABLE VI-continued

| Chemotactic Factor | ΔF (Hz) | Average ΔF (Hz) |
|---|---|---|
| $10^{-5}$M FMP | 2470 | 4465 |
|  | 6460 |  |
| $10^{-6}$M FMP | 5348 | 4484 |
|  | 3621 |  |
| $10^{-7}$M FMP | 1891 | 1352 |
|  | 814 |  |

These data show that the cells are responding to the presence of chemotactic factor in a dose-response like manner and that this response can be measured by cell adherency as determined by a change in frequency of a quartz crystal oscillator.

What is claimed is:

1. A method for the direct quantitative measurement of adherent cells in a liquid sample comprising the steps of:
    a. contacting said liquid sample with the surface of a piezoelectric oscillator having a premeasured resonant frequency;
    b. incubating said sample and said oscillator for a sufficient period of time to allow said cells to contact said surface;
    c. washing and drying said oscillators; and
    d. determining the change in frequency of said oscillator from said premeasured frequency.

2. The method according to claim 1 wherein said oscillator is a quartz crystal.

3. The method according to claim 1 wherein said cells are leukocytes derived from peripheral blood.

4. The method according to claim 3 wherein said leukocytes are selected from the group consisting of granulocytes and mononuclear cells.

5. The method according to claim 1 wherein said cells are derived from a source selected from the group consisting of lymph nodes and fluid, thymus, spleen and peritoneal exudate.

6. The method according to claim 1 wherein said cells are fibroblasts.

7. The method according to claim 1 further comprising the step of pretreating said oscillator with autologous serum prior to step a.

8. The method according to claim 1 further comprising the step of adding autologous serum to said liquid sample prior to step a.

9. The method according to claim 1 wherein said liquid sample contains fetal calf serum.

10. The method according to claim 1 wherein said oscillator has a layer of a positively charged material applied thereto prior to step a.

11. The method according to claim 10 wherein said positively charged material is poly(2-hydroxy-3-dimethylamino-1,4-butane).

12. The method according to claim 1 wherein said oscillator has a layer of a negatively charged material applied thereto prior to step a.

13. The method according to claim 12 wherein said negatively charged material is gum arabic.

14. The method according to claim 1 wherein said oscillator has a layer of polystyrene applied thereto prior to step a.

15. The method according to claim 1 wherein said oscillator has a layer of an antigen applied thereto prior to step a.

16. The method according to claim 15 wherein said antigen is selected from the group consisting of viral antigens, parasitic antigens, fungal antigens, tumor antigens, antigenic products of viruses, antigenic products of parasites, antigenic products of fungi, antigenic products of tumors, and plant derived lectins.

17. The method according to claim 15 wherein said antigen is selected from the group consisting of contact dermatitis antigens and autoimmune disease-associated antigens.

18. The method according to claim 15 wherein said antigen is a microbial antigen.

19. A method for the direct quantitative measure of chemotaxis comprising the steps of:
    a. placing at least one drop of liquid sample containing a chemotactic agent on the surface of a piezoelectric oscillator having a premeasured resonant frequency;
    b. covering said drop with a porous membrane;
    c. placing at least one drop of a liquid sample containing cells over said membrane;
    d. allowing the product of steps a-c to incubate for a sufficient period of time to allow said cells to migrate through said membrane to surface of said oscillator;
    e. removing said porous membrane;
    f. washing and drying said oscillator; and
    g. determining the change in frequency of said oscillator from said premeasured frequency.

20. The method according to claim 19 wherein said cells used in step c are leukocytes derived from peripheral blood.

21. The method according to claim 19 wherein said cells are derived from a source selected from the group consisting of lymph nodes and fluid, thymus, spleen and peritoneal exudate.

22. A method for the direct quantitative measurement of phagocytosis comprising to steps of:
    a. contacting a liquid sample containing cells and a predetermined number of particles with the surface of a piezoelectric oscillator having a premeasured resonant frequency;
    b. incubating said sample and said oscillator for a sufficient period of time to allow said cells to contact said surface;
    c. washing and drying said oscillators; and
    d. determining the change in frequency of said oscillator from said premeasured frequency.

23. The method according to claim 22 wherein said liquid sample contains autologous serum.

24. The method according to claim 22 wherein said particles are selected from the group consisting of zymosan starch and polystyrene latex.

* * * * *